United States Patent [19]

Wong

[11] 4,451,454

[45] May 29, 1984

[54] PROPHYLAXIS AND TREATMENT OF THROMBOEMBOLIC DISORDERS IN MAN AND IN WARM-BLOODED ANIMALS WITH BICARBONATE SALTS OF ALKALI METALS

[76] Inventor: Dennis W. Wong, 2853 Sunnyglen Rd., Torrance, Calif. 90505

[21] Appl. No.: 274,386

[22] Filed: Jun. 16, 1981

[51] Int. Cl.³ .............................................. A61K 33/00
[52] U.S. Cl. ...................................... 424/127; 424/19; 424/31
[58] Field of Search ............................ 424/127, 19, 31

[56] References Cited

U.S. PATENT DOCUMENTS 3,857,949  12/1974  Garzia ................................ 424/317

OTHER PUBLICATIONS

Wong, D. et al., *JAMA*, 244(1), 61–62 (1980).
Wong, D., *J. Pharm. Sci.*, 69(8), 978–980 (Aug. 1980).

*Primary Examiner*—Richard A. Schwartz

[57] ABSTRACT

Sodium bicarbonate and potassium bicarbonate are systemic anticoagulants that when administered internally inhibit blood coagulation in man and in warm-blooded animals. As such, they are useful and effective in the treatment and/or prevention of thromboembolic diseases, myocardial infarction or other conditions associated with high risk of thromboembolism. Sodium bicarbonate is especially useful for preventing clotting of ptient's blood during kidney dialysis and for preserving citrated human or animal whole blood and plasma indefinitely under proper storage conditions.

15 Claims, No Drawings

PROPHYLAXIS AND TREATMENT OF THROMBOEMBOLIC DISORDERS IN MAN AND IN WARM-BLOODED ANIMALS WITH BICARBONATE SALTS OF ALKALI METALS

BACKGROUND OF THE INVENTION

It has been more than four decades since the introduction of heparin, warfarin and indandione derivatives for the treatment and preventing of thromboembolic disorders. These drugs remain to be the only effective anticoagulants in use today. They exert their effects by inhibiting either the action of or the formation of one or more clotting factors. Since the inactivity of even a single clotting factor is considered a disease, these drugs in effect creating a clotting defect resembling that of certain clinical conditions. Consequently, serious untoward effects are commonly associated with the uses of heparin and other oral anticoagulants. Hemorrhage is the outstanding toxic effect, and may occur even with therapeutic doses. In light of this, the physician must employ proper caution in the use of these drugs because the range between inefficient therapy and undue hemorrhagic risk is narrow and varies considerably from patient to patient. Individualized treatment and frequent clinical observation are imperative for patients on anticoagulant therapy. Serious adverse reactions resulting from drug interaction with other medications have been reported.

Sodium bicarbonate is widely used as a therapeutic agent for the treatment of respiratory or metabolic acidosis. The usual therapeutic does of sodium bicarbonate is in the range of 1-2 mEq/kg body weight and is normally administered intravenously as a 7.5% hypertonic solution or as a 1.5% isotonic solution. Orally, it is used as an antacid, urine alkalizing agent to enhance the renal excretion of certain drugs and topically as a lavage. Commercially, it is the main ingredient in baking powder, effervescent salts and beverages as chief source of carbon dioxide. Until the recent discovery of its anticoagulant action on blood coagulation (Wong, DW, et al., JAMA 244(1):61, 1980) sodium bicarbonate has long been regards as a safe and effective therapeutic agent relatively free of serious side effects. With the exception of overdose-induced seizures or tetany secondary to hypocalemia and hyperalkalosis, no other known adverse reactions have been reported.

Therapeutically, potassium bicarbonate has very limited medical application. It is classified primarily as gastric antacid or as potassium supplement. The usual oral dose is 1-8 g/day given in divided doses. Potassium ions when systemically absorbed exerts potent action on the heart resulting cardiac failure. The drug itself has little value in combating metabolic acidosis because the potassium ions cannot replace sodium as the cation of the extracellular fluid.

SUMMARY OF THE INVENTION

Experimental results and clinical patient data have confirmed the findings that sodium bicarbonate and potassium bicarbonate exert a potent anticoagulant action on the blood clotting process. Although the exact mechanism of clot inhibition is unclear, it appears that they exert their effects by direct inhibition of the conversion of fibrinogen to fibrin clot without interfering with other clotting factors. The relative safety and nontoxic nature of these bicarbonate salts make them ideal anticoagulants for the treatment and/or prevention of thromboembolic diseases replacing other more toxic drugs.

A therpeutic composition containing sodium bicarbonate or potassium bicarbonate may be administered to human patients and other warm-blooded mammals by the oral, rectal or parenteral routes particularly in combination with a pharmaceutically acceptable excipient. They may be formulated as substained release or enteric-coated capsules or tablets, suppositories and injectable ampules. The effective therapeutic dosage of sodium or potassium bicarbonate should be individualized according to the needs of the patients as determined by standard laboratory clotting assays. Potassium bicarbonate may be substituted for sodium bicarbonate if sodium salt is contraindicated or if patient has prior history of cardiovascular diseases such as congestive heat failure or hypertension.

Sodium citrate potentiates the anticoagulant action of sodium bicarbonate and potassium bicarbonate. It can be added to the bicarbonate therapeutic regiment to obtain a more potent therapeutic effect. Special precaution is warrented to prevent overdose-induced hemorrhage and hypocalemia.

Sodium and potassium bicarbonate are pharmacologically and therapeutically compatible with other anticoagulants. They can be given concurrently with heparin, or other oral agents such as warfarin or indandione derivatives. Sodium bicarbonate is specially useful for preventing clotting during renal dialysis and as a preservative in extending the useful shelf life of citrated human whole blood and plasma beyond the current twenty-one day period.

DETAILED DESCRIPTION OF THE INVENTION

This invention relates to a novel physiobiological property of sodium bicarbonate and potassium bicarbonate discovered by the present inventor. When systemically absorbed, these bicarbonate salts exert potent inhibitory action on blood coagulation. The objective of the present invention is to use the bicarbonate salts for the prophylaxis and treatment of thromboembolic disorders in man or in warm-blooded animal. A second object is to prevent clotting of patient's blood during renal dialysis by adding an anticoagulant effective amount of either sodium or potassium bicarbonate to the dialysis fluid. A third objective is to use sodium bicarbonate to preserve citrated human whole blood and plasma.

Blood coagulation or thrombosis is a highly complex multifacet biological phenomenon. It involves a serious of biochemical and enzymatic reactions and the interaction of many different clotting proteins, enzymes and co-factors. The final result is the formation of fibrin clot and prevention of hemorrhage.

Conveniently, blood coagulation may be considered in terms of three basic reactions; namely, as follows: (1) The formation of autoprothrombin C; (2) The formation of thrombin, and (3) the formation of fibrin clot as a result of the enzymatic action of thrombin acted on fibrinogen, a clotting protein normally present in the blood. These biochemical reactions may be expressed as follows:

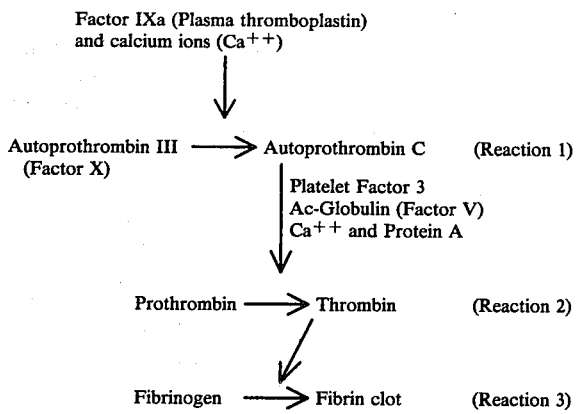

Any of the above reactions can be interrupted by a numbers of inhibitors, anticoagulants or by lacking a clotting factor due to genetic defect.

Sodium bicarbonate and potassium bicarbonate exert potent inhibitory action on blood coagulation. In vitro experimental results using normal human whole blood and pure human fibrinogen have demonstrated that both sodium and potassium bicarbonate interfere with the clotting process (Wong DW, et al., JAMA 244(1):61, 1980 and Wong DW, J. Pharm. Sci. 69(8): 978, 1980). Addition of either of these bicarbonate salts to normal blood samples causes prolongation in clotting as measured by two standard laboratory clotting assays: the prothrombin time (PT) and thrombin clotting time (TCT). This biochemical reaction is concentration dependent, that is, clot inhibition is directly proportional to the amount of either sodium or potassium bicarbonate presented in the blood samples.

The onset of the anticoagulant action of the bicarbonate salts was observed to be immediate and rose sharply with increasing amount of the salt added to the normal blood samples. Both PT and TCT were elevated in comparison with control samples containing neither sodium or potassium bicarbonate (See Table 1 and 2).

Table 1 illustrates the potent anticoagulant action of sodium bicarbonate on normal human blood sample in vitro as measured by PT and TCT determinations.

Table 2 summarizes the in vitro PT and TCT data on human blood samples containing various amount of potassium bicarbonate added.

Table 3 demonstrates changes occur in the clotting process in patients who have been treated for acute acidosis with sodium bicarbonate infusion.

TABLE I

The in vitro anticoagulant action of sodium bicarbonate on fresh human blood samples. The amount of sodium bicarbonate added to the samples is ranged from 12.5–125 mEq/L of blood assuming an average adult blood volume of 65 mg/Kg body weight. Plasma ionic strength ($\mu$) = 0.154. Average of three determinations from 3 normal healthy volunteers.

| SAMPLES | Sodium bicarbonate concentration | | | | PROTHROMBIN TIME (sec.) | THROMBIN CLOTTING TIME (sec.) |
|---|---|---|---|---|---|---|
| | mEq/Kg body wt. | mEq/ml blood | Total $\mu$ | pH | | |
| Control | 0.00 | 0.0000 | 0.154 | 7.40 | 11.1 | 7.5 |
| 1 | 0.81 | 0.0125 | 0.167 | 7.40 | 11.3 | 8.1 |
| 2 | 1.62 | 0.0250 | 0.179 | 7.40 | 11.8 | 9.0 |
| 3 | 2.43 | 0.0375 | 0.192 | 7.50 | 12.3 | 9.5 |
| 4 | 3.24 | 0.0500 | 0.204 | 7.65 | 13.3 | 10.5 |
| 5 | 4.05 | 0.0625 | 0.217 | 7.65 | 14.1 | 12.1 |
| 6 | 4.86 | 0.0750 | 0.229 | 7.65 | 15.3 | 14.0 |
| 7 | 5.67 | 0.0875 | 0.242 | 7.65 | 17.0 | 16.5 |
| 8 | 6.48 | 0.1000 | 0.254 | 7.65 | 19.8 | 18.0 |
| 9 | 7.29 | 0.1125 | 0.267 | 7.70 | 22.5 | 21.0 |
| 10 | 8.10 | 0.1250 | 0.279 | 7.74 | 26.0 | 32.0 |

TABLE II

The effect of potassium bicarbonate on human blood coagulation in vitro as determined by prothrombin and thrombin clotting time assays. The average blood volume of a 70 kg adult is assumed to be 65 ml/kg body weight. (n = 3)

| SAMPLES | POTASSIUM BICARBONATE CONCENTRATION | | | | PROTHROMBIN TIME (sec.) | THROMBIN CLOTTING TIME (sec.) |
|---|---|---|---|---|---|---|
| | mEq/kg body wt. | mEq/ml of blood | Total $\mu$ | pH | | |
| Control | 0.00 | 0.00 | 0.154 | 7.6 | 10.9 | 8.6 |
| 1 | 0.65 | 0.01 | 0.164 | 7.6 | 10.6 | 9.7 |
| 2 | 1.30 | 0.02 | 0.174 | 7.6 | 11.1 | 10.3 |
| 3 | 1.95 | 0.03 | 0.184 | 7.6 | 11.2 | 11.4 |
| 4 | 2.60 | 0.04 | 0.194 | 7.7 | 12.1 | 12.9 |
| 5 | 3.25 | 0.05 | 0.204 | 7.8 | 13.3 | 21.4 |
| 6 | 3.90 | 0.06 | 0.214 | 7.8 | 14.1 | 23.0 |
| 7 | 4.55 | 0.07 | 0.224 | 7.8 | 14.9 | 24.3 |
| 8 | 5.20 | 0.08 | 0.234 | 7.9 | 15.8 | 30.8 |
| 9 | 5.85 | 0.09 | 0.244 | 7.9 | 17.4 | 35.0 |
| 10 | 6.50 | 0.10 | 0.254 | 8.0 | 20.0 | 42.9 |

TABLE III

Correlation of change in prothrombin time with bicarbonate infusion in acute acidosis.

| | Before Bicarbonate Therapy | | | | | | After Bicarbonate Therapy | | | | | | |
|---|---|---|---|---|---|---|---|---|---|---|---|---|---|
| Patient | Blood pH | $HCO_3$, mEq | $P_{O_2}$, mm Hg | $P_{CO_2}$, mm Hg | PT, s* | PTT, s* | Total $HCO_3$ injected, mEq | Blood pH | $HCO_3$, mEq | $P_{O_2}$, mm Hg | $P_{CO_2}$, mm Hg | PT, s* | PTT, s* |
| 1 (severe metabolic acidosis) | 6.76 | 7 | 68 | 55 | 10.7 (10.6) | 35.5 (29.7) | 223.0+ | 7.39 | 15 | 140 | 20 | 20.2 (10.6) | 54.3 (29.2) |
| 2 (cardiopulmonary arrest) | 7.40 | 17 | 28 | 96 | 14.3 (10.6) | 83.4 (32.4) | 89.2 | 7.23 | 20 | 52 | 74 | 16.1 (10.5) | 93.8 (32.4) |
| 3 (diabetic ketoacidosis) | 7.02 | <5 | 65 | 18 | 12.2 (10.6) | 38.2 (36.0) | 89.2 | 7.27 | 15 | 382 | 32 | 22.9 (10.6) | 58.4 (35.5) |
| 4 (septic shock and lactic acidosis) | 7.14 | <8 | 83 | 20 | 13.0 (10.6) | 38.8 (34.9) | 89.2 | 6.98 | 8 | 136 | 19.3 | 28.2 (10.0) | 47.3 (32.0) |

*Normal values for prothrombin time (PT) and partial thromboplastin time (PTT) are given in parentheses.
+Blood samples were collected 15 minutes after intravenous infusion-a total of 223 mEq in 11 hours.

Clinical data obtained from patients who received intravenous administration of sodium bicarbonate support the in vitro findings. Although many variables affect the clotting process in vivo, over the short period of time these observations were made, the most striking consistant changes were in $P_{O_2}$ and bicarbonate concentration in response to administration of oxygen and massive intravenous dose of bicarbonate. In each case, the PT and partial thromboplastin time (PTT) became prolonged in comparison with the base line value prior to sodium bicarbonate therapy (See Table 3). Additionally, it has been found by the present inventor that sodium bicarbonate inhibits the in vitro conversion of pure human fibrinogen to fibrin clot. In the same report, sodium citrate is shown to potentiate the anticoagulant effect of sodium bicarbonate (Wong DW, J. Pharm. Sci. 69(8): 978, Aug. 1980). While sodium citrate concentration remains constant in the pure fibrinogen samples, the addition of sodium bicarbonate causes a marked increase in TCT. In blood, sodium citrate prevents clotting by reacting with serum calcium ions($Ca^{++}$) forming an undissociated calcium citrate complex. Without $Ca^{++}$ ions, coagulation will not occur. However, in a pure fibrinogen system where $Ca^{++}$ ions are absent, the synergistic action of sodium citrate with sodium bicarbonate can only be explained as result of an increase in ionic strength in the samples in addition to the effect of sodium bicarbonate.

Although an increase in pH had been recorded with increase amount of $NaHCO_3$ or $KHCO_3$ in the blood samples and pure fibrinogen samples, this study did not demonstrate a linear relationship between the rise in pH and the sharp increase in PT and TCT.

Although not wish to be bound by theory, the inhibitory action of sodium and potassium bicarbonate on blood coagulation appears to be due primarily to the anion bicarbonate($HCO_3^-$) chemical species, an increase in ionic strength and to a lesser extend the effect of pH. It is well known that some neutral salts retard the coagulation process and others accelerate the conversion of fibrinogen to fibrin. Both cations and anions may bind to the fibrinogen or fibrin molecules during the process of clot formation and, depending upon the individual chemical species, can either accelerate or inhibit coagulation. The degree of clot inhibition is also greatly affected by the concentration and the ionic strength of the salt is question. Previous studies have revealed that the structure and properties of fibrin clots are greatly modified by variation of pH and ionic strength during coagulation. However, even at constant pH and ionic strength, certain ions and neutral molecules at low concentration exert a profound change on the structure of the fibrin clot and on the rate of its formation.

In man or warm-blooded animal, it has been established that blood coagulation is cybernetic, with fibrin deposition and subsequent lysis taking place as a continuous process. The incidence of normal hemostasis as compared to increased fibrin deposition(thrombosis), or increased fibrinolysis(hemorrhage), depends upon a delicate balance between the procoagulant system and associated inhibitions, the fibrinolytic system and its inhibitors.

Three delicately interslated hemostatic elements are involved: the vasculature, the platelets, and the blood protein system comprised not only of coagulation proteins but also containing the fibrinolytic, complement, and kinin systems. The cybernetic system is being constantly driven toward fibrin deposition, while the inhibitors ensure that, normally, thrombosis will not occur.

The leading cause of pulmonary and cerebral embolism is thrombophlebitis. Thromboembolism is caused by abnormalities of the blood vessel, the blood or the circulation resulting the formation of blood clots called thrombi. Within a short period of time, many of these blood clots become dislodged from the blood vessels and migrate freely as emboli via the circulation into the lung. These emboli are then trapped and cause serious complications interfering with normal circulation and gas exchange.

Formation of blood clots occurs frequently in myocardial infarction. Recent experimental findings have confirmed the existence of fibrin or clot deposits at the sites of infarcts. Because of microvascular damage or injury, the coagulation process is initiated in the early or acute phase of the disease resulting in a well formed fibrin gel surrounding the injured or infarcted tissue. The fibrin clot effectively cuts off blood supply to the area of infarction and further aggravates the patient's symptoms.

Other conditions which are associated with a high risk of venous thromboembolism include the postoperative period; pregnancy, particularly the postpartum period; endocarditis and congestive heart failure; chronic pulmonary disease; fractures or other injuries of the lower extremities; chronic deep venous insufficiency of the legs; prolonged bed rest and carcinoma.

Management of thromboembolic diseases is determined by two considerations:

(1) the degree to which the circulation has been comprised; and (2) the nature history of the disease. In time, most emboli will resolve. Therefore, the goals of therapy should be to sustain life until clot resolution can occur, and to prevent embolic recurrence. In most instances, medical therapy with anticoagulant drugs is adequate. With hospitalized patient, heparin is currently the drug of choice.

Heparin inhibits thrombin formation and thromboplastin generation in the plasma. Considerable side effects and toxicity are associated with the use of heparin injection. Hemorrhage is a constant concern and may occur even at low dosage. Side effects such as anorexia, nausea, vomitting, diarrhea and urticaria are common. Acute reversible thrombocytopenia, alopecia, severe asthma, rhinitis and fever have been encountered. Interaction of heparin with other medications such as aspiring, antihistamine and antibiotics are common and often lead to serious complications. The drug is ineffective orally, but it is well absorbed after intramuscular or subcutaneous injection. Because of short duration of actiion, it should be administered by intermitten intravenous therapy or by continuous intravenous drip method. Patients on heparin therapy must be hospitalized and required close observation and frequent monitoring for blood clotting changes.

Oral anticoagulants such as warfarin and indandione derivatives are agents of choice for ambulatory patients and patients on maintenance dosage regiment. These drugs exert potent anticoagulant effect by interfering with and by depressing the formation of various essential clotting factors. Normal prothrombin synthesis is inhibited as well as the production of clotting factor II, IX, and X following oral administration of these drugs. In man, absorption of these drugs from the gastrointestinal tract is slow and erratic. The onsert of action is long with a latent period of 12-24 hours. The duration of action may persist for 4-5 days. Warfarin and indandione derivatives are potent anticoagulants with severe toxic reactions. Patients or these medications must be under closed and frequent observation to prevent over dose. (Goodman LA and Gilman A. The Pharmacological Basis of Therapeutics. 3rd edition, MacMillan, New York 1965)

The aim of anticoagulant therapy is, of course, to impede the coagulation or clotting mechanism to such an extent that thrombosis will not occur, but at the same time avoiding spontaneous bleeding and serious complications. Sodium bicarbonate and potassium bicarbonte satisfy these requirements. Both drugs have been used medicinally for many decades. At therapeutic dosage level, no known serious side effects or adverse reactions have been reported.

In addition, the bicarbonate salts have many advantages over existing anticoagulants. These include: (1fast onset of action; (2) they act directly on the clotting mechanism by inhibiting the conversion of fibrinogen to fibrin clot and do not effect other clotting factors; (3) they do not interact with other medications resulting harmful side effects or complications; (4) in addition to their anticoagulant action, they help to maintain blood electrolytes level and acid-base balance; (5) these drugs are well absorbed by the gastrointestinal tract and can be given orally, rectally or by parenteral route; (6) they do not cause antigenic or hypersensitivity reactions; (7) the therapeutic dosage of the bicarbonate salts can be individualized according to the needs of the patient; and (8) they are safe and non-toxic.

Sodium bicarbonate and potassium bicarbonate are safe and effective therapeutic agents for the treatment and/or prevention of thromboembolism replacing existing anticoagulants. Similar to currently available drugs, the bicarbonates can not dissolve preformed or existing clots but will prevent embolic recurrence. Prophylactic use of either sodium or potassium bicarbonate will prevent the occurrence of thromboembolic diseases such as pulmonary or cerebral embolism, myocardial infarction or other conditions associated with high risk of venous thrombosis such as surgery, pregnancy, endocarditis, congestive heat failure, orthopedic injuries or carcinoma.

Of current medical interest is the use of sodium bicarbonate injection in place of heparin in renal dialysis. Anticoagulant is essential during kidney dialysis. Small amount of heparin injection is required and is normally added to the dialysis fluid to prevent clotting of patient's blood. However, uncontrollable hemorrhage frequently occurs after dialysis at the infusion site. Since the therapeutic dosage of sodium bicarbonate is much easier to control than heparin, the problem of drug induced bleeding is thus eliminated. Additionally, the use of sodium bicarbonate injection will reduce the incidence of renal acidosis and shock.

Another important medical application of sodium bicarbonate is in the preservation of human whole blood and plasma for blood transfusion. Citrated whole human blood and plasma are important blood volume replenishers. The blood is drawn from selected donor under rigid aseptic precaution and is collected into a sterile container containing anticoagulant acid citrate dextrose solution(ACD). The purpose of the sodium citrate in the ACD formulation is to prevent initial blood clotting during the collection process. However, it will not prevent the blood or plasma from further deterioration even under proper storage condition. The ACD solution extends the useful life of the red cells in the whole blood with the result that the blood can be used with safety for a period of three weeks after collection. At the end of 21 days, they must be discarded. Clotting will occur due to the presence of procoagulant proteins normally found in the blood. The addition of 0.05-2% sodium bicarbonate to the ACD formulation will prevent autocoagulation thus extending the useful shelf life of the citrated whole human blood or plasma indefinitely under proper storage conditions. The optimal amount of $NaHCO_3$ required to preserve these blood replenishers can be determined by routine experiment by those who are skilled in the art.

The dosage of sodium bicarbonate or potassium bicarbonate will vary depending upon known factors such as the age, weight and health of the recipient; the route of administration; nature and extend of symptoms, kind of concurrent treatment, frequency of treatment, and the therapeutic effect desired. The effective therapeutic dosage of these drugs must be individualized according to the needs of each patient as determined by standard laboratory clotting assays such as PT, TCT and PTT. In patients with acute episode of thromboembolism, sodium or potassium bicarbonate injection should be used to produce prompt therpeutic response. The usual parenteral dose is 0.05-4 mEq(5-350 mg)/kg body weight normally administered intravenously in a 1-10% isotonic or hypertonic solution. Therpeutically, sodium bicarbonate injection is preferred over potassium bicarbonate solution. However, the latter may be used in place of sodium bicarbonate if sodium salt is contraindicated of if patient has prior history of cardiovascular disease. Special precaution is warranted to prevent potassium intoxication.

A sterile apyrogenic parenteral composition suitable for administration by injection is prepared by dissolving 1-50% by weight of either sodium or potassium bicarbonate powder or crystals in water for injection, U.S.P. or other pharmaceutically acceptable carriers such as 0.9% sodium chloride solution, dextrose solution or the likes. In addition, the parenteral solution can contain suitable preservatives, stabilizing agents or buffer substances. The preferred parenteral solution is 1-10% of sodium or potassium bicarbonate dissolved in water for injection having a pH of 7.4 to 8.5.

Orally, sodium and potassium bicarbonate are well absorbed by the gastrointestinal tract. However, both salts are partially inactivated by gastric acid and rapidly converted to carbon dioxide and related chloride salts. Excess sodium or potassium bicarbonate is then systemically absorbed through the gastric mucosa. The ability of these bicarbonates to neutralize stomach acid is the principal reason for their efficacy as gastric antacids but less efficient as systemic anticoagulants. In order for the bicarbonate salts to exert their anticoagulant effect, they must be systemically absorbed in the original chemical state.

In addition to parenteral administration, therapeutic compositions containing sodium or potassium bicarbonate may be given to patients or warm-blood animals by the oral or rectal routes, particularly in combination with a pharmaceutically acceptable excipients, carriers, binders and the likes. They may be formulated as tablets, capsules, pills, dragees or preferably as sustained-release or enteric-coated capsules or tablets that resist solution in the stomach but disintegrate and release their medication in the intestine. Gastric inactivation is thus avoided and the drug is being effectively absorbed in the intestine.

Rectal administration of either sodium or potassium bicarbonate in the form of suppositories is equally effective. They are readily absorbed through the rectal mucosa. Suppositories contain the active ingredient in a suitable oleaginous or water-soluble base. The oleaginous class includes cocoa butter and fats with similar properties; the water-soluble materials include polyethylene glycols.

Suitable pharmaceutical carriers, binders, excipients and the likes for the preparation of solid dosage forms and parenteral solutions are described in Remington's Pharmaceutical Sciences, A. Osol, 16th edition, 1980, a standard reference test in this field.

The usual oral or rectal dosage of sodium or potassium bicarbonate for the treatment and/or prevention of thromboembolic diseases is 1-20 g/day given in divided dose. However, the effective therapeutic dose must be individualized according to the clinical condition and health of the patient, the desired therapeutic response and the maintenance dosage required to prevent thromboembolism.

The pharmaceutical compositions in solid dosage forms according to the invention generally contain from 0.1 to 99.5%, usually from 0.5-95% of the active ingredient by weight of the total composition depending on the mode of administration. Each capsule, tablet or suppository may be formulated to contain from 50 mg to 2 grams of either sodium or potassium bicarbonate plus other pharmaceutically acceptable excipients.

The pharmaceutical compositions may also contain other pharmaceutically and therapeutically compatible active principles.

Useful pharmaceutical dosage forms for administration of sodium or potassium bicarbonate of this invention are given below by way of illustration only and not by way of limitation:

(1) Substained release or enteric-coated capsules or tablets, each contains from 50 mg to 2000 mg of either sodium bicarbonate or potassium bicarbonate plus pharmaceutically acceptable excipients.

(2) Capsules, tablets, pills or dragees each contains from 50 mg to 2000 mg of either sodium bicarbonate or potassium bicarbonate plus pharmaceutically acceptable excipients.

(3) Rectal suppositories each contains 50 mg to 2000 mg of either sodium bicarbonate or potassium bicarbonate plus suppository excipients.

(b 4) A parenteral composition suitable for intravenous administration is prepared by dissolving 1-10% by weight of either sodium or potassium bicarbonate in water for injection, USP. The solution is sterilized by conventional means.

(5) Capsules, tablets, pills or dragees each contains from 50 mg to 2000 mg of sodium bicarbonate and 50 mg to 2000 mg of sodium citrate plus pharmaceutically acceptable excipients.

(6) Substained release or enteric-coated capsules or tablets each contains 50 mg to 2000 mg of sodium bicarbonate and 50 mg to 2000 mg of sodium citrate plus pharmaceutically acceptable excipients.

(7) Rectal suppositories each contains 50 mg-2000 mg of sodium bicarbonate and 50 mg-2000 mg of sodium citrate plus suppository excipients.

(8) A sterile non-pyrogenic injection suitable for parenteral administration containing 1-10% sodium bicarbonate and 1-10% sodium citrate dissolved in water for injection, USP.

(9) Capsules, tablets, pills or dragees each contains from 50 mg-2000 mg of potassium bicarbonate and 50 mg-2000 mg of sodium citrate plus pharmaceutically acceptable excipients.

(10) Substained release or enteric-coated capsules or tablets each contains 50 mg-2000 mg of potassium bicarbonate and 50 mg-2000mg of sodium citrate plus pharmaceutically acceptable excipients.

(11) Rectal suppositories each contains from 50 mg to 2000 mg of potassium bicarbonate and 50 mg to 2000 mg of sodium citrate plus suppository excipients.

(12) A parenteral composition suitable for administration by injection contains 1-10% potassium bicarbonate and 1-10% sodium citrate dissolved in water for injection, USP.

The above examples and the described procedures are for illustrative purposes only and are not intended to be limiting of the scope of the invention. It will be apparent to those skilled in the art that both may be modified within the scope of the invention defined in the following claims.

I claim:

1. A pharmaceutical composition for the prophylaxis and treatment of thromboembolic disorders in man or in warm-blooded animals which comprises an anticoagulant effective amount of a bicarbonate salt of an alkali metal in combination with a pharmaceutically acceptable carrier, binder or excipient, said bicarbonate salt being selected from the group consisting of sodium bicarbonate and potassium bicarbonate.

2. A pharmaceutical composition of claim 1 in a form suitable for parenteral administration comprising 1-50% by weight of said active ingredient together with a pharmaceutically acceptable carrier.

3. A pharmaceutical composition of claim 2 as an aqueous solution containing 1-10% by weight of said active ingredient.

4. A pharmaceutical composition of claim 1 in a form suitable for systemic absorption by oral or rectal administration comprising 0.1-95% by weight of said active ingredient together with a pharmaceutically acceptable binder or excipient.

5. A pharmaceutical composition of claim 4 in the form of sustained-released or enteric-coated tablets, capsules, pills, dragees or in suppository form containing 50-2000 mg of said active ingredient per dosage unit.

6. A pharmaceutical composition for prophylaxis and treatment of thromboembolic disorders in man or in warm-blooded animals which comprises as active ingredients an anticoagulant effective amount of a bicarbonate salt of an alkali metal and a therapeutically effective amount of sodium citrate in admixture with a pharmaceutically acceptable carrier, binder or excipient, said bicarbonate salt being selected from the group consisting of sodium bicarbonate and potassium bicarbonate.

7. A pharmaceutical composition of claim 6 in the form suitable for parenteral administration comprising 1-50% by weight of said active ingredients together with a pharmaceutically acceptable carrier.

8. A pharmaceutical composition of claim 7 is an aqueous solution containing 1-10% by weight of a bicarbonate salt of an alkali metal as defined in claim 6 and 1-10% by weight of sodium citrate together with a pharmaceutically acceptable carrier.

9. A pharmaceutical composition of claim 6 in the form suitable for systemic absorption following oral or rectal administration comprising 0.1-95% by weight of said active ingredients together with a pharmaceutically acceptable binder or excipient.

10. A pharmaceutical composition of claim 9 in the form of sustained-released or enteric-coated tablets, capsules, pills, dragees or in suppository form containing 50-2000 mg of a bicarbonate salt of an alkali metal as defined in claim 6 and 50-2000 mg of sodium citrate per dosage unit together with a pharmaceutically acceptable binder or excipient.

11. A method of prevention of blood coagulation in man or in warm-blooded animals which comprises administering internally to said host a bicarbonate salt of an alkali metal at a dose of 0.05-4 mEq(5-350 mg)/kg body weight, said bicarbonate salt being selected from the group consisting of sodium bicarbonate and potassium bicarbonate.

12. A method of prophylaxis and treatment of thromboembolic disorders or conditions associated with thromboembolism in man or in warm-blooded animals which comprises administering interally of said host a bicarbonate salt of an alkali metal at a dosage range of 0.05-4 mEq(5-350 mg) per kg body weight based on the age, weight and health of the recipient, said bicarbonate salt being selected from the group consisting of sodium bicarbonate and potassium bicarbonate.

13. A method of prophylaxis and treatment of thromboembolic disorders or conditions associated with thromboembolism in man or in warm-blooded animals which comprises coadministering internally to said host a bicarbonate salt of an alkali metal at a dose range of 0.05-4 mEq (5-350 mg) per kg body weight and a therapeutic effective amount of sodium citrate based on the age, weight and health of the recipient, said bicarbonate salt being selected from the group consisting of sodium bicarbonate and potassium bicarbonate.

14. A method of prevention of blood coagulation during kidney dialysis which comprises adding to the dialysis fluid an anticoagulant effective amount of a bicarbonate salt of an alkali metal prior to kidney dialysis based on the age, weight and health of the recipient, said bicarbonate salt being selected from the group consisting of sodium bicarbonate and potassium bicarbonate.

15. A method of preservation of human or animal whole blood and plasma which comprises admixing with acid citrate dextrose solution 0.05-2% of a bicarbonate salt or an alkali metal in a blood collection container, said bicarbonate salt being selected from the group consisting of sodium bicarbonate and potassium bicarbonate.

* * * * *